United States Patent [19]

Stroz et al.

[11] 4,374,122

[45] Feb. 15, 1983

[54] METHOD OF REDUCING DENTAL CARIES

[75] Inventors: John J. Stroz, Monroe, Conn.; Donald A. M. Mackay, Pleasantville, N.Y.

[73] Assignee: Nabisco Brands, Inc., New York, N.Y.

[21] Appl. No.: 248,088

[22] Filed: Mar. 27, 1981

[51] Int. Cl.³ .......................... A61K 7/16; A61K 9/68
[52] U.S. Cl. .......................................... 424/48; 426/3; 426/548; 424/49; 424/180; 424/361; 424/246
[58] Field of Search ............................... 426/548, 3–6; 424/48–58

[56] References Cited

U.S. PATENT DOCUMENTS

| | | | |
|---|---|---|---|
| 3,932,606 | 1/1976 | Barth et al. | 424/52 |
| 4,132,772 | 1/1979 | Barth et al. | 424/52 |
| 4,158,068 | 6/1979 | Lipinski et al. | 426/548 |
| 4,208,431 | 6/1980 | Friello et al. | 426/3 |
| 4,256,730 | 3/1981 | Benedict | 424/49 |
| 4,277,464 | 7/1981 | Reussner et al. | 424/49 |

OTHER PUBLICATIONS

Hough et al., Developments in Sweetners-1, pp. 151-158 "A Survey of Less Common Sweetners" Applied Science Publishers, Ltd, Barking, Essex, England.

Primary Examiner—Shep K. Rose
Attorney, Agent, or Firm—Richard Kornutik

[57]  ABSTRACT

A method for treating teeth to reduce caries is provided wherein the teeth are contacted with an anti-caries compound comprising 3,4-dihydro-6-methyl-1,2,3-oxathiazine-4-one-2,2-dioxide or the sodium, ammonium, potassium or calcium salt thereof, optionally in the presence of a sugar, for example, as contained in a chewing gum composition or toothpaste or powder composition, the anti-caries compound being present in an amount sufficient to inhibit growth of *Streptococcus mutans* in the oral cavity or on the teeth.

9 Claims, No Drawings

METHOD OF REDUCING DENTAL CARIES

The present invention relates to a method for preventing or reducing dental caries wherein 3,4-dihydro-6-methyl-1,2,3-oxathiazine-4-one-2,2-dioxide or its sodium, potassium, ammonium or calcium salt is employed to inhibit growth of *Streptococcus mutans* in the oral cavity.

Foods containing natural sugars such as sucrose and glucose have long been recognized as a major contributing cause of dental caries. The sugars are an easily utilizable source of nutrition for bacteria, such as *Streptococcus mutans* found in the oral cavity, which bacteria is responsible for the formation of plaques on the surface of the teeth due to dextran and levan production from sucrose. The levan-containing plaques absorb further amounts of sugar and thus provide a ready source of nutrition for bacteria adjacent the surface of the teeth even while the host is asleep. The bacteria acting on the residue sugar or levan in the plaques results in fermentation and rapid transformation of the sugar or levan into acids which, upon reaching the "critical" pH of 5.50, dissolve the minerals of the teeth.

In an effort to reduce tooth decay, artificial sweeteners, such as saccharin salts and cyclamate salts have been employed as sugar substitutes in many foods. However, such foods have not been entirely accepted by the consuming public, and especially by children, because of the metallic or bitter after-taste characteristic of the usual forms of artificial sweeteners. The use of non-fermentable carbohydrates, such as polyhydric alcohols like sorbitol, mannitol and xylitol have been employed in place of sugars in chewing gums and confections. Moreover, these non-sugar bulking agents have been found to be physically inferior in taste, stability, and manufacturing ease to the sugar normally used.

It has now been found that the use of 3,4-dihydro-6-methyl-1,2,3-oxathiazine-4-one-2,2-dioxide or its sodium salt, potassium salt (Acesulfame-K), calcium or ammonium salt in foods, confections, chewing gum, beverages and the like as a natural sugar substitute or in combination with natural sugars, as well as in toothpaste, powder or polishing compositions, provides an especially effective tool in the fight against dental caries and prevention and inhibition of tooth decay. Surprisingly and unexpectedly, the 3,4-dihydro-6-methyl-1,2,3-oxathiazine-4-one-2,2-dioxide or its sodium, potassium, ammonium or calcium salt has been found to inhibit growth of *Streptococcus mutans* strains of bacteria, such as *Streptococcus mutans* 10449, a prime contributor to formation of dental plaque and tooth decay.

Thus, in accordance with the present invention, a method is provided for treating teeth to inhibit or prevent caries, wherein the teeth are contacted with 3,4-dihydro-6-methyl-1,2,3-oxathiazine-4-one-2,2-dioxide or a water-soluble salt thereof, such as the sodium or potassium salt (Acesulfame K) or the calcium or ammonium salt, in an amount sufficient to inhibit growth of *Streptococcus mutans* strains present in the oral cavity or on the teeth. In a preferred embodiment, the above potassium salt (also known generically as acetosulfame-potassium salt) is employed. However, where employed, the term "3,4-dihydro-6-methyl-1,2,3-oxathiazine-4-one-2,2-dioxide" will also include its water-soluble salts, such as the sodium, potassium, ammonium or calcium salt.

The 3,4-dihydro-6-methyl-1,2,3-oxathiazine-4-one-2,2-dioxide, and its sodium, potassium and calcium salts are known sweeteners and are disclosed in U.S. Pat. No. 4,158,068.

In carrying out the method of the invention, the 3,4-dihydro-6-methyl-1,2,3-oxathiazine-4-one-2,2-dioxide will usually be employed in conjunction with a non-toxic edible carrier to form a food, confection, chewing gum, dental tablet, cream or paste, beverage and the like. Regardless of the form of the composition or carrier, the total amount of the 3,4-dihydro-6-methyl-1,2,3-oxathiazine-4-one-2,2-dioxide present in the composition will preferably be beyond the normal organoleptic threshold of sweetness and thus may be employed in amounts ranging from about 0.05 to about 5% or more by weight, and preferably from about 0.1 to about 1% by weight of the total composition.

It appears that the effectiveness of the 3,4-dihydro-6-methyl-1,2,3-oxathiazine-4-one-2,2-dioxide in inhibiting plaque formation increases with increasing teeth exposure or contact time. Thus, the presence of relatively small amounts of the active ingredient solubilized in the saliva over extended periods of time (for example, 1 to 900 mg over a period of 5, 10, 20, 30 minutes or more) is, for the purposes of the present invention, more desirable than the presence of large or peak amounts solubilized in the saliva for relatively short periods of time (for example, 1 to 900 mg over a period of 1 to 4 minutes). Thus, the 3,4-dihydro-6-methyl-1,2,3-oxathiazine-4-one-2,2-dioxide will preferably be provided in a form or composition so that it may be controlledly or slowly released and solubilized in relatively small quantities in the saliva over extended periods of time; moreover, although large amounts may be initially present, at any given time, amounts of the active ingredient which are organoleptically acceptable (that is, below the undesirably oversweet threshold) will be solubilized in the saliva and available for tasting.

Regardless of the form of the composition containing the active ingredient, whether it be a chewing gum or otherwise, as will be seen herein, the 3,4-dihydro-6-methyl-1,2,3-oxathiazine-4-one-2,2-dioxide may be preferably employed in combination with a natural sugar, such as sucrose or glucose. Inasmuch as the sugar, by itself, contributes to formation of dental plaque, the active ingredient may be said to function as an antiplaque antidote to sugar and inhibit plaque formation. The natural sugar may be present in an amount ranging from about 90 to about 0.05%, preferably from about 90 to about 40%, and more preferably from about 85 to about 70% by weight of the final product.

In a preferred embodiment of the present invention, the 3,4-dihydro-6-methyl-1,2,3-oxathiazine-4-one-2,2-dioxide will be employed together with sucrose or other natural sugar in a weight ratio of active ingredient:sugar of within the range of from about 1:10 to about 1:200, and preferably from about 1:30 to about 1:150. The presence of the sugar apparently enhances adhesion of the active ingredient to the tooth surface.

The term "natural sugar" includes sugar alcohols, such as xylitol, sorbitol or mannitol as well as one or more sugars or sugar containing materials, for example, monosaccharides, disaccharides and polysaccharides, some examples of which follow:

monosaccharides of 5 or 6 carbon atoms, such as arabinose, xylose, ribose, glucose, mannose, galactose, fructose, dextrose, or sorbose or mixtures of two or more of the foregoing monosaccharides;

disaccharides, such as sucrose such as cane or beet sugar, lactose, maltose or cellobiose; and polysaccharides, such as partially hydrolyzed starch, dextrin or corn syrup solids.

Of course, the 3,4-dihydro-6-methyl-1,2,3-oxathiazine-4-one-2,2-dioxide need not be employed with the sugar; sugar consumed separately from the 3,4-dihydro-6-methyl-1,2,3-oxathiazine-4-one-2,2-dioxide or even sugar produced by breakdown of starches from previous means may contribute to growth of *Streptococcus mutans*. In any event, the 3,4-dihydro-6-methyl-1,2,3-oxathiazine-4-one-2,2-dioxide will inhibit growth of certain strains of *Streptococcus mutans* regardless of whether it is employed with sugar.

As indicated, the 3,4-dihydro-6-methyl-1,2,3-oxathiazine-4-one-2,2-dioxide may be incorporated into a chewing gum.

The preferred chewing gum composition suitable for use in the method of the present invention comprises a chewing gum wherein the 3,4-dihydro-6-methyl-1,2,3-oxathiazine-4-one-2,2-dioxide is employed in combination with a natural sugar, such as sucrose or in a sugarless gum with sorbitol and/or a hydrogenated starch hydrolysate (HSH) as disclosed in U.S. Pat. No. 26,959 and U.S. Pat. No. 3,566,811, other sugar alcohols, such as mannitol and/or xylitol, and/or gum arabic. The active ingredient will be employed in a weight ratio to the sugar alcohol (or HSH) of within the range of from about 1:10 to about 1:200, preferably from about 1:30 to about 1:150, and more preferably from about 1:50 to about 1:100 and in a weight ratio to the sugar (where present) of within the range of from about 1:10 to about 1:200, and preferably from about 1:50 to about 1:100. Such preferred compositions contain from about 0.05 to about 5% by weight of active ingredient and preferably from about 0.1 to about 1% by weight active ingredient, and the sugar alcohol (or HSH) is present in an amount within the range of from about 10 to about 75%, and preferably from about 10 to about 65% by weight and/or a natural sugar, such as sucrose in an amount within the range of from about 50 to about 90%, and preferably from about 70 to about 85% by weight.

In one embodiment of the invention, sorbitol syrup or solution may also be employed in a weight ratio of sorbitol powder:sorbitol solution of within the range of from about 6:1 to about 2:1.

In general, the sorbitol syrup may be present in an amount to provide from about 0 to about 10% by weight sorbitol and preferably from about 1 to about 8% sorbitol based on the weight of the final chewing gums. Use of the sorbitol in the form of the syrup or solution increases moisture content and thus softness of the gum.

The chewing gum employed in the method of the invention may be prepared by mixing melted gum base (heated at, for example, 160°-170° F.) and color, if desired, adding polyol, such as mannitol, to the mix, and mixing for 1-5 minutes, adding sucrose and/or sorbitol (in the form of powder), and 3,4-dihydro-6-methyl-1,2,3-oxathiazine-4-one-2,2-dioxide, softener, such as lecithin, flavor, and glycerin (where employed), and when a smooth mixture is obtained, optionally, adding sorbitol solution or corn syrup, then adding gum arabic, and then optionally adding spray-dried flavor and mixing the entire mass for 2 to 5 minutes.

If desired, the above may be mixed with one or more easily extractable water-soluble food acid and/or flavors. The resulting mix is then formed into sticks or tablets of chewing gum employing conventional techniques.

Examples of sugarless gum formulations which may be employed in the method of the present invention are as follows:

|  | Parts by Weight |
| --- | --- |
| Gum base | 20–30 |
| Mannitol | 3–12 |
| 1,3-Dihydro-6-methyl-1,2,3-oxathiazine-4-one-2,2-dioxide | 0.05–3 |
| Sorbitol | 40–65 |
| Softner (lecithin) | 0–1.5 |
| Glycerin | 0–3 |
| Flavor | 0.3–2 |

Examples of sugar-containing formulations which may be employed in the method of the present invention are as follows:

|  | Parts by Weight |
| --- | --- |
| Gum base | 17–30 |
| Sucrose | 50–85 |
| 1,3-Dihydro-6-methyl-1,2,3-oxathiazine-4-one-2,2-dioxide | 0.05–3 |
| Softener (lecithin) | 0–1.5 |
| Flavor | 0.3–2 |

Other examples of preferred chewing gums for use in the method of the invention are set out in U.S. Pat. No. 4,208,431 the disclosure of which is incorporated herein by reference.

The following in vitro tests were carried out to show that 3,4-dihydro-6-methyl-1,2,3-oxathiazine-4-one-2,2-dioxide (in the form of its potassium salt-Acesulfame-K) inhibits growth of *Streptococcus mutans*:

Microorganisms

Both *Streptococcus mutans* strain 6715-9 and *S. mutans* 10449 are cariogenic human isolates whose virulence has been determined in a variety of animal models. Streptococcal cultures were grown at 37° C. then stored at room temperature in Fluid Thioglycollate Medium and transferred every ten days. All experiments were performed at 37° C.

Composition of Growth Media

All growth media components purchased from Difco Laboratories, Detroit, MI.

(i) Fluid Thioglycollate Medium
  Bacto fluid thioglycollate—29.8 grams/liter
  Bacto beef extract—12.0 grams/liter $CaCO_3$—0.5 grams/culture tube (10 ml)

(ii) Jordan's Medium
  Bacto tryptone—5.0 grams/liter
  Bacto yeast extract—5.0 grams/liter
  Potassium phosphate, dibasic—5.0 grams/liter
  Glucose—2.5 grams/liter (iii) Mitis Salivarius Agar
  Bacto Mitis Salivarious Agar—90 grams/liter
  Bacto Chapman Tellurite—1.0 ml/liter Streptococcal Growth Streptococcal growth was determined by monitoring the turbidity of cultures grown in Jordan's Medium at 650 nm using either a Gilford Model 300-N or a Bausch and Lomb Spectronic 20 spectrophotometer.

Glucose Uptake Studies

Glucose uptake was measured using steptococcal intact cell suspensions of the following composition:

Streptococcal cells—2.0 ml (1:100 dilution=$A_{650\,nm}$ of 0.10)
Potassium phosphate, 0.01 M, pH 6.2–1.0 ml
Jordan's Medium—1.0 ml
Glucose—420 μmoles
Acesulfame-K—0—2.0% final concentration
Distilled water to a total volume of 6.0 ml The 6.0 ml cell suspensions were incubated under a nitrogen atmosphere at 37° C. and 0.5 ml samples removed at various times and analyzed for their glucose content using the Worthington Statzyme 500 method.

The following results were observed.

(i) Acesulfame-K reduced the growth yield of *S. mutans* strains 6715-9 and 10449 when they were grown at 37° C. for fourteen hours in liquid Jordan's Medium. Both *S. mutans* strains are human isolates whose virulence has been established in animal models. All subsequent studies were done with *S. mutans* strain 10449 since it is currently being used in many other dental research laboratories.

(ii) Acesulfame-K lowered the growth yield of *S. mutans* strain 10449 when grown in liquid Jordan's Medium at 37° C. for fourteen hours when either 0.5% sucrose or 0.5% glucose was used as the primary energy source.

(iii) The ability of Acesulfame-K to lower the growth yield of *S. mutans* strain 10449 was independent of the glucose concentration in the liquid Jordan's Medium.

(iv) The ability of Acesulfame-K to lower the growth yield of *S. mutans* strain 10449 was much more dramatic when the organism was grown on Mitis-Salivarius agar plates for forty-eight hours. Acesulfame-K not only reduced colony size but served to alter colonal morphology as well.

(v) Acesulfame-K also had a negative effect upon the growth rate of *S. mutans* when grown in liquid Jordan's Medium. However, the effect of Acesulfame-K upon the twenty-four hour growth yield was not nearly as great as that observed after only fourteen hours.

On the basis of the data observed, it may be considered that Acesulfame-K does interact in a negative manner with *S. mutans*. Specifically, Acesulfame-K decreases the growth rate of *S. mutans* strain 10449 in liquid culture but appears to have a much less dramatic effect on decreasing the growth yield of a twenty-four four culture as compared to a culture grown for only fourteen hours. In contrast the growth yield of this organism was markedly decreased when it was grown for forty-eight hours on Mitis-Salivarius Agar plates.

The following Examples illustrate preferred embodiments of the present invention without, however, limiting the same thereto. All temperatures are expressed in °F.

EXAMPLE 1

A cherry flavor sugar-containing chewing gum is prepared from the following ingredients:

| Ingredients | Parts by Weight |
| --- | --- |
| Gum base | 20 |
| Sugar | 50 |
| Corn syrup | 16 |
| Dextrose | 10 |
| Lecithin | 0.2 |
| Citric acid | 0.5 |
| Fumaric acid | 2 |
| 3,4-Dihydro-6-methyl-1,2,3-oxathiazine-4-one-2,2-dioxide, potassium salt | 0.2 |
| Artificial cherry flavor | 1 |
| Gum arabic coated cherry flavor | 1.5 |

The gum base is melted (temperature 270°) and placed in a standard dough mixer kettle equipped with sigma blades. The corn syrup and lecithin are added and mixed for 2 minutes at 200°. At the time the mix is folding well, powdered 3,4-dihydro-6-methyl-1,2,3-oxathiazine-4-one-2,2-dioxide, potassium salt and powdered fumaric acid are added to the base-syrup mix and the mixture is mixed for 1 minute at 200°. Thereafter, the sucrose, dextrose, flavor oil, citric acid and coloring agents are added and blended with the above mixture for 5 minutes at 160°. The resulting gum is discharged from the kettle and formed into gum sticks employing conventional techniques.

The chewing gum product obtained is found to have a pleasant balanced sweet-sour taste for up to 30 minutes and is effective in inhibiting growth of *Streptococcus mutans* in the oral cavity.

EXAMPLE 2

A peppermint flavor sugar-containing chewing gum is prepared from the following ingredients:

| Ingredients | Parts by Weight |
| --- | --- |
| Gum base | 20 |
| Corn syrup, 44° Be' | 17 |
| 3,4-Dihydro-6-methyl-1,2,3-oxathiazine-4-one-2,2-dioxide, potassium salt | 0.2 |
| Powdered sugar (sucrose) | 50 |
| Dextrose | 10 |
| Peppermint oil | 1 |
| Lecithin | 0.2 |

The gum base is melted (temperature 270°) and placed in a standard dough mixer kettle equipped with sigma blades. The corn syrup and lecithin are added and mixed for 2 minutes at 200°. At the time the mix is folding well, powdered 3,4-dihydro-6-methyl-1,2,3-oxathiazine-4-one-2,2-dioxide, potassium salt is added and the mixture is mixed another 3 minutes at 200°. Thereafter, the sucrose, dextrose and flavor oil are added during which time the mixture is mixed another 3 minutes at 200°. Thereafter, the sucrose, dextrose and flavor oil are added during which time the mixture is mixed for 5 minutes. The gum is then discharged from the kettle, cut into 25 lb. loaves and allowed to cool to 90°–120° F. It is then rolled to a thickness of 0.178 cm on a standard Gimpel machine and scored into strips of 7.26 cm wide and 41.9 cm long, and cooled for 12–18 hours.

The chewing gum product obtained is found to have a pleasant sweet taste for up to 30 minutes and inhibits growth of *Streptococcus mutans* in the oral cavity.

EXAMPLE 3

A spearmint flavor sugar-containing chewing gum is prepared from the following ingredients:

| Ingredients | Parts by Weight |
| --- | --- |
| Gum base | 20 |

| Ingredients | Parts by Weight |
| --- | --- |
| Sugar (sucrose) | 52 |
| Corn syrup 44° Be' | 17 |
| Dextrose | 10 |
| Lecithin | 0.2 |
| 3,4-Dihydro-6-methyl-1,2,3-oxathiazine-4-one-2,2-dioxide, potassium salt | 0.2 |
| Spearmint oil | 0.6 |

The gum base is melted (temperature 270°) and placed in a standard dough mixer kettle equipped with sigma blades. The corn syrup and lecithin are added and mixed for 2 minutes at 200°. At the time the mix is folding well, powdered 3,4-dihydro-6-methyl-1,2,3-oxathiazine-4-one-2,2-dioxide, potassium salt and flavor oil are mixed for 1 minute at 200°. Thereafter, the sucrose, dextrose and coloring agents are added and blended with the above mixture for 5 minutes at 160°. The resulting gum is discharged from the kettle and formed into gum sticks as described in Example 1.

The chewing gum product obtained is found to have a pleasant sweet taste for up to 30 minutes and inhibits growth of *Streptococcus mutans* in the oral cavity.

EXAMPLE 4

A spearmint flavor sugar-containing chewing gum is prepared from the following ingredients:

| Ingredients | Parts by Weight |
| --- | --- |
| Gum base | 18.5 |
| 3,4-Dihydro-6-methyl-1,2,3-oxathiazine-4-one-2,2-dioxide, potassium salt | 0.2 |
| Chalk | 3.3 |
| Sugar | 49 |
| Corn syrup | 17 |
| Lecithin | 0.2 |
| Sorbitol | 10 |
| Spearmint flavor (oil) | 1 |
| Spearmint (spray-dried) | 0.5 |

The gum base is melted at 140°–150° F. and chalk premixed with 3,4-dihydro-6-methyl-1,2,3-oxathiazine-4-one-2,2-dioxide, potassium salt is added and the mixture mixed in a standard dough mixer equipped with sigma blades. Sugar is added and mixed for 3 minutes at 200°. Thereafter, liquid flavor is added and mixed for 2 minutes, a premix of lecithin and corn syrup is added and mixed for 3 minutes, sorbitol is added and mixed for 1 minute and spray-dried flavor is added and mixed for 1 minute. The resulting gum is discharged from the kettle and formed into gum sticks employing conventional techniques.

The chewing gum product obtained is found to have a pleasant balanced sweet taste for up to 30 minutes and is effective in inhibiting growth of *Streptococcus mutans* in the oral cavity.

What is claimed is:

1. A method of treating teeth to reduce or prevent caries by inhibiting growth of *Steptococcus Mutans* in the presence of fermentable carbohydrates in the oral cavity, which comprises contacting the teeth with an anti-caries compound comprising 3,4-dihydro-6-methyl-1,2,3-oxathiazine-4-one-2,2-dioxide or a water-soluble salt thereof in conjunction with a carrier which includes sugar to form a composition containing from about 0.05 to about 5% by weight anti-caries compound whereby the incidence of caries is inhibited or prevented in comparison to the incidence of caries expected as a result of inclusion of sugar in said composition.

2. The method as defined in claim 1 wherein said water-soluble salt is the sodium, potassium, ammonium or calcium salt.

3. The method as defined in claim 1 wherein said water-soluble salt is the potassium salt.

4. The method as defined in claim 1 wherein said composition comprises a chewing gum composition.

5. The method as defined in claim 4 wherein said composition includes a sugar in an amount of from about 40 to about 90% by weight of said gum.

6. A method of treating teeth to inhibit formation of dental plaques and caries, which comprises contacting the teeth with an anti-caries compound comprising 3,4-dihydro-6-methyl-1,2,3-oxathiazine-4-one-2,2-dioxide or its sodium, ammonium, potassium or calcium salt thereof in an amount sufficient to inhibit growth of *Streptococcus mutans* in the oral cavity or on the teeth and thereby inhibit formation of dental caries, said anti-caries compound being employed in conjunction with a sugar containing carrier to form an anti-caries composition containing from about 0.05 to about 5% anti-caries compound.

7. The method as defined in claim 6 wherein said anti-caries compound is employed in the form of its potassium salt.

8. The method as defined in claim 6 wherein said composition comprises a chewing gum composition.

9. A method of inhibiting the growth of *Streptococcus mutans*, which consists essentially of the step of contacting *Streptococcus mutans* with sugar and 3,4-dihydro-6-methyl-1,2,3-oxathiazine-4-one-2,2-dioxide or its sodium, potassium, ammonium or calcium salt in amounts sufficient to inhibit growth of *Streptococcus mutans*.

* * * * *